United States Patent

Graiver et al.

Patent Number: 5,429,839
Date of Patent: Jul. 4, 1995

[54] METHOD FOR GRAFTING PREFORMED HYDROPHILLIC POLYMERS ONTO HYDROPHOBIC POLYMER SUBSTRATES

[75] Inventors: Daniel Graiver; Toshiyuki Okada; Samir D. Serrano, all of Midland, Mich.

[73] Assignee: Mizu Systems, Midland, Mich.

[21] Appl. No.: 93,548

[22] Filed: Jul. 19, 1993

Related U.S. Application Data

[63] Continuation-in-part of Ser. No. 852,451, Mar. 16, 1992, abandoned.

[51] Int. Cl.⁶ .............................................. B65B 33/00
[52] U.S. Cl. ..................................... 427/155; 427/302; 427/322; 427/393.5; 524/577; 525/58
[58] Field of Search ................... 427/155, 2, 302, 322, 427/393.5; 524/577; 525/58

[56] References Cited

U.S. PATENT DOCUMENTS

| | | | |
|---|---|---|---|
| 4,047,908 | 9/1977 | Steigelmann et al. | 210/500 X |
| 4,100,309 | 7/1978 | Micklus et al. | 427/2 |
| 4,589,964 | 5/1986 | Mayhem et al. | 522/85 |
| 4,897,433 | 1/1990 | Sago et al. | 427/2 X |
| 4,968,532 | 11/1990 | Janssen et al. | 427/164 |
| 5,143,949 | 9/1992 | Grogan et al. | 427/155 X |

*Primary Examiner*—Michael Lusignan
*Attorney, Agent, or Firm*—Robert L. McKellar

[57] ABSTRACT

Coatings of hydrophilic organic polymers such as polyvinyl alcohol are grafted to substrates formed from hydrophobic organic polymers and polyorganosiloxanes by exposing the surface of the substrate to an aqueous solution of the hydrophilic poller in the presence of a solubilized compound of tetravalent cerium that preferably contains hydroxyl or amino groups as ligands.

3 Claims, No Drawings

METHOD FOR GRAFTING PREFORMED HYDROPHILLIC POLYMERS ONTO HYDROPHOBIC POLYMER SUBSTRATES

This is a continuation-in-part of application Ser. No. 07/852,451 filed on Mar. 16, 1992, now abandoned.

BACKGROUND OF THE INVENTION

1. Field of the Invention

This invention relates to a method for grafting a preformed hydrophilic polymer such as polyvinyl alcohol onto the surface of hydrophobic organic polymer substrates. This invention also relates to coated organic polymer substrates prepared using this method.

2. Background Information

It is known to apply coatings of various materials onto the surface of substrates formed from hydrophobic polymers. Coatings of liquid or gel type lubricating materials are particularly desirable for tubing and catheters that are inserted into blood vessels and various body cavities in animals and humans, for medical devices such as surgical gloves, sutures, contact lenses, cardiac pacemakers and associated leads, artificial implants, and peristaltic pump chambers.

One type of lubricating coating is temporary, and includes non-reactive oils such as vegetable oils and silicone oils (typically low molecular weight polydiorganosiloxanes). The disadvantage of these coatings include their temporary nature and the tendency of the coatings to rub off and stain materials they come in contact with.

Methods for applying a more permanent hydrophilic coatings to hydrophobic substrates are also known. Japanese Patent Publication (Kokai) no. 60/171140 describes filling the pores of a polymerized perfluorohydrocarbon polymer with a water-soluble monomer such as 2-hydroxyethyl methacrylate that is subsequently polymerized and crosslinked in situ. Treatment of a polyurethane substrate with a salt to produce a porous structure, filling the pores with gelatin and crosslinking the gelatin using glutaraldehyde is taught in an article by L. Rhode that appeared in Wiss. Z. Wilhelm-Pieck-Univ. Rostock, Naturwiss Reihe, 33 (7), 14–18, 1984.

A method for increasing the durability of hydrophilic coatings using an interpenetrating polymer network is described by M. Dror et al. in Biomater., Med. Devices, Artif. Organs, 7(1), 31–9, 1979. The network is formed by dissolving a crosslinkable polymer in a solvent capable of swelling the substrate, exposing the substrate to the resultant solution and then crosslinking the polymer when it has been absorbed into the swollen substrate. A major disadvantage of this technique is that it requires use of organic solvents, which typically adversely alters the physical properties of the substrate in addition to the recovery and/or disposal problems associated with the use of organic solvents.

Hydrophilic coatings can be covalently bonded to hydrophobic substrates if the inert surface of the substrate is first activated by exposure to a hydrogen plasma or high energy radiation and then reacted with at least one water soluble monomer. As an example of this technique, Japanese patent publication 75/38790 published in 1975, teaches exposing a polyvinyl chloride substrate to ionizing radiation in the presence of a mixture of oxygen and ozone to form oxides and peroxides that are used as active sites for the graft polymerization of 2-hydroxyethyl methacrylate.

The use of radiation from a $^{60}Co$ source to initiate the graft polymerization of a water soluble monomer such as 2-hydroxyethyl methacrylate, N-vinyl pyrrolidinone and ethylene glycol dimethacrylate on to a silicone rubber substrate is described in German patent 2,515,671, which issued in 1975.

B. Rattner in published German patent application No. 2,515,671 teaches using radiation to graft polymerize various acrylic monomers onto the surface of silicone rubber in the presence of cupric nitrate.

The disadvantages of using high energy radiation to initiate graft polymerization of a monomer onto a substrate are the cost of the equipment required to generate the radiation. The radiation may also cause sub-surface damage to the substrate, thereby adversely affecting its physical properties.

One way to avoid the use of high energy radiation is to use a coupling agent containing groups that form covalent or other types of bonds with a subsequently formed hydrophilic polymer. S.C. Lin et al. in Adv. Biomater., (Clin. Appl. Biomater) 4, 245–52 (1985) teach treating a silicone rubber substrate with vinyltriacetoxysilane which was then copolymerized with N-vinyl pyrrolidone to form a coating that was not only adsorbed onto the surface of the substrate but also absorbed into it.

The use of isocyanate groups to bond hydrophilic polymers to hydrophobic substrates is disclosed in U.S. Pat. No. 4,100,309, which issued on Aug. 29, 1978, and U.S. Pat. No. 4,876,126, which issued to Takemura et al. on Oct. 24, 1989. The high reactivity and toxicity of the isocyanate group make its presence undesirable in medical devices and equipment.

PCT International Patent Application WO84/00908 teaches using a solubilized 2-hydroxyethyl methacrylate/methacrylic acid copolymer and an unvulcanized surgical glove that had previously been primed using aluminum sulfate, and then vulcanizing the glove.

Graft polymerization on to hydrophobic substrates of various monomers forming hydrophilic polymers is also described in the following references:

Seifert et al. in the Journal of Biomaterials Research, 19, 9, 1043–71 (1985) using copolymers of 2-hydroxyethyl methacrylate and N-vinylpyrrolidone;

Bamford et al. in Eur. Poly. Journal, 19, 1027–35 (1983) using a hydrogel-forming monomer in the presence of the combination of an N-bromo- or N-chloroamide or -imide and a transition metal carbonyl;

Chapiro in Eur. Poly. Journal, 19, 859–61 (1983) using radiation-induced grafting of N-vinylpyrrolidone;

Jendrychouska-Bonamour in J. Poly. Sci, Polym. Chem. Ed., using radiation-induced grafting of acrylic acid onto a poly(methyl methacrylate) substrate, followed by reaction of the resultant copolymer with carbodiimide or glutaraldehyde;

Beach et al. in a US Government report (NIH -N01-HV-4-2950-6) using $^{60}Co$ radiation to graft the sodium salt of a crotonic acid/vinylacetate copolymer from a solution of the corresponding monomers; and J. Kearney et al. in the Am. Chem. Soc., Div. Org. Coat. Plast. Chem., Pap., 33 (2), 346–50, (1973) using an aqueous solution of acrylamide, a crosslinking agent and a transition metal salt as the polymerization catalyst to prevent homopolymerization in the solution.

It is known that ceric salts, particularly double salts containing amino and/or nitro groups, will initiate polymerization of vinyl monomers such as the esters monomers of acrylic and methacrylic acids. This reaction is believed to involve formation of peroxides and was first investigated by G. Mino and S. Kaizerman reporting in the Journal of Polymer Science, 31, 242-3 (1958). The use of a ceric salt as an initiator to graft polymerize acrylamide onto pulp is described in German patent no. 2,416,531, which issued during 1974.

Amudeswari et al. in Curr. Sci. 52, 2, 58-9 (1983) describe the graft polymerization 2-hydroxyethyl methacrylate on to a powdered collagen using a cerium compound as the initiator.

Xin et al in Makromol. Chemie, 186, 8, 1533-41 (1985) used acrylamide or the combination of tetramethylene glycol and a polyfunctional carboxylic acid as the monomer(s) and a polyurethane as the substrate. The monomer was polymerized using a ceric salt as the polymerization initiator.

The conditions of the graft polymerization reactions described in the foregoing references using ceric compounds as the polymerization initiator result in substantial amounts of homopolymerization in addition to crosslinking and grafting of the polymer onto the surface of the substrate. In the absence of a means to control the homopolymerization, the properties of the final coating could vary substantially, depending upon relative rates of the competing polymerization and grafting reactions.

The homopolymers not grafted to the substrate together with unreacted monomers typically must be removed from the coated substrate, particularly if the final product is intended for use as a medical device.

The preparation substrates coated with hydrophilic polymers and control of the properties exhibited by these substrates would be considerably easier if it were possible to graft a preformed polymer to the surface of substrate rather than trying to reproducibly balance the competing homopolymerization and grafting reactions.

The present inventors discovered that this desirable goal can be achieved by contacting a hydrophobic organic polymer containing polar groups such as hydroxyl, carboxylate and urethane, or a polyorganosiloxane with an aqueous solution of certain hydrophilic organic polymers in the presence of certain ceric compounds.

SUMMARY OF THE INVENTION

The present invention provides a method for grafting a coating of a hydrophilic organic polymer on to solid substrates formed from hydrophobic organic polymers or polyorganosiloxanes. The method involves contacting the substrate with an aqueous solution of a hydrophilic polymer in the presence of a ceric compound containing hydroxyl or nitrogen-containing groups as ligands under conditions that will graft said polymer to the surface of the substrate. The resultant coating cannot be removed by washing the substrate with water and retains excellent bonding to the substrate following immersion of the coated substrate in water for up to six months or longer. The presence of a coating on the surface of the substrate has been confirmed using infrared spectroscopy and electron photomicroscopy, in-vitro protein adsorption and blood platelet adhesion.

This invention also provides aqueous hydrophilic coating compositions for hydrophobic substrates formed from organic polymers or polyorganosiloxanes. The compositions consist essentially of an aqueous solution comprising a solubilized organic hydrophilic polymer and a solubilized ceric compound in an amount sufficient to promote grafting of said polymer to the substrate.

DETAILED DESCRIPTION OF THE INVENTION

This invention provides an aqueous coating composition for solid substrates formed from hydrophobic polymers selected from the group consisting of organic polymers and polyorganosiloxanes, said composition comprising A. a solubilized hydrophilic organic polymer containing a plurality of non-terminal hydroxyl or amino groups and substantially free of ethylenic unsaturation, and B. a solubilized compound of tetravalent cerium containing at least one ligand selected from the group consisting of hydroxyl and amino, where the concentration of said compound in said solution is sufficient to promote grafting of said hydrophilic organic polymer to the surface of said substrate as a uniform coherent coating without agglomerating said hydrophilic organic polymer, and C. a quantity of water sufficient to achieve the desired viscosity of said composition.

This invention also provides a method for grafting a coating of preformed hydrophilic organic polymer onto the surface of a hydrophobic substrate selected from the group consisting of organic polymers and polyorganosiloxanes, said method comprising exposing at least one surface of said substrate to an aqueous composition comprising A. a solubilized hydrophilic organic polymer containing a plurality of non-terminal hydroxyl or amino groups and substantially free of ethylenic unsaturation, and B. a solubilized compound of tetravalent cerium, and C. a quantity of water sufficient to achieve the desired viscosity, where the concentration of said compound in said solution and the conditions of said exposure are sufficient to graft said hydrophilic polymer to the surface of said substrate as a uniform, coherent coating without agglomerating said hydrophilic polymer.

The characterizing feature of the present method is the ability to use a preformed hydrophilic organic polymer rather than the corresponding monomer(s) as the coating material for a hydrophobic substrate. This feature is believed to result from the ability of the cerium compound to graft the hydrophilic polymer to the surface(s) of the substrate.

The Hydrophilic Organic Polymer

1. Polyvinyl Alcohol

Polyvinyl alcohol is a preferred hydrophilic polymer based on the cost and availability of this material. Polyvinyl alcohol is typically prepared by hydrolysis or saponification of a polymerized ester of the alcohol, such as vinyl acetate. The degree to which the resultant polymer is hydrolyzed will depend upon the intended end use of the polymer. The vinyl alcohol polymers used as hydrogel precursors in accordance with the present method are preferably at least 90 percent hydrolyzed.

The degree of branching and concentration of 1,2-glycol linkages in the polymer are considered to be of secondary importance with regard to their effect on the processability of the present solutions and the physical properties of the final coatings. A linear configuration within the polymer molecules is preferred to achieve the maximum degree of hydrogen bonding and desirable surface characteristics in the final coated substrate.

The molecular weight of the polyvinyl alcohol affects the viscosity of the initial polymer solution and the properties of the coating formed by grafting the polymer to the surface of the substrate in accordance with the present method.

Keeping these considerations in mind, any of the commercially available grades of polyvinyl alcohol can be used to prepare coatings in accordance with the present method. These polymers are classified according to molecular weight as high (above about 86,000), medium (40,000 to 52,000) and low (14,000). A molecular weight range of from 80,000 to 115,000 is preferred.

The polyvinyl alcohol used in accordance with the present method is not crosslinked using reactants that form covalent bonds.

The optimum concentration range of polyvinyl alcohol in the solution used to prepare grafted coatings in accordance with the present method is dependent upon the molecular weight of the polymer, the temperature of the solution, reaction time, and the equipment used to apply the coating onto the hydrophobic substrate.

The present inventors found that coatings exhibiting acceptable levels of physical properties are not obtained when the concentration of polyvinyl alcohol in the initial solution is below about 1 percent by weight.

The useful upper limit for the concentration of polyvinyl alcohol is determined at least in part by the viscosity of the solution and the capabilities of the equipment used to prepare the solution and coat it on the substrate. Using the preferred molecular weight range of from 80,000 to 115,000 the upper limit of polymer concentration appears to be 20 weight percent. Polymer concentrations of from 2 to about 12 percent are preferred.

2. Other Hydrophilic Polymers

While water soluble polyvinyl alcohol is a preferred hydrophilic polymer, other water-soluble natural and synthetic polymers can be utilized as hydrophilic polymers in the present coating compositions if they contain a plurality of hydrophilic groups such as hydroxyl, amido, carboxyl, amino, ammonium or sulfonyl ($-SO_3-$).

Suitable hydrophilic polymers include but are not limited to starch, polysaccharides and related cellulosic polymers; polyalkylene glycols and oxides such as the polyethylene oxides; polymerized ethylenically unsaturated carboxylic acids such as acrylic, methacrylic and maleic acids and partial esters derived from these acids and polyhydric alcohols such as the alkylene glycols; homopolymers and copolymers derived from acrylamide; and homopolymers and copolymers of vinylpyrrolidone.

The type of hydrophilic polymer selected will determine the physical properties of coated substrate prepared in accordance with the present method. Properties including but not limited to lubricity, adsorption of proteins, including blood platelets, plasma deposition and durability of the coating will be influenced by the chemical composition, molecular weight, degree of branching, and crystallinity of the grafted hydrophilic polymer.

The Hydrophobic Substrate

The substrates to which hydrophilic polymers are grafted in accordance with the present method include hydrophobic organic polymers and polyorganosiloxanes. As used in this specification hydrophobic implies that the contact angle between water and the surface of the substrate is more than about 90°.

Organic polymers useful as substrates include the following classes of polymers:

Polyolefins such as polyethylene, polypropylene, polystyrene, polybutadiene and elastomeric copolymers of butadiene, styrene and acrylonitrile;

Polymers derived from fluorinated olefins such as tetrafluoroethylene,

Condensation type polymers such as and polyurethanes and siloxane-urethane copolymers; and Naturally occurring hydrophobic polymers such as rubber;

Polyorganosiloxanes are polymeric materials characterized by repeating siloxane groups, represented by $R_aSiO_{4-a/2}$, where R is a monovalent substituted or unsubstituted hydrocarbon radical and time value of a is 1 or 2. The degree of polymerization and the crosslink density will determine the appearance and physical properties of the polymer, which can be a liquid, gel, elastomer or resin.

Preferred substrates include natural and synthetic elastomers. Natural rubber and elastomers formed from polyurethanes and polydiorganosiloxanes characterized by the repeating unit $R_2SiO$, where R is defined in the preceding paragraph, are particularly preferred. In these polydiorganosiloxanes both R radicals are typically methyl or one is methyl and the other is phenyl or 3,3,3-trifluoropropyl. Polydiorganosiloxane elastomers, also referred to as silicone rubber, are sufficiently well known to those skilled in this art that a detailed description of these materials and methods for preparing them are not required.

The present method is particularly suitable for grafting coatings of preformed hydrophilic polymers to fabricated articles such as tubing, catheters, surgical gloves, sutures, artificial implants, other medical devices and surgical equipment formed from natural or synthetic elastomers. It has been shown that coatings of the preferred hydrophilic polymers on these substrates increase the lubricity of the surface. In many instances, particularly using the preferred polyvinyl alcohol coatings, the adsorption of proteins and the adhesion of blood platelets are substantially reduced.

The Cerium Compound

Published studies of the mechanism associated with grafting reactions catalyzed by cerium salts indicate that any of the water soluble ceric compounds capable of forming complexes with oxygen atoms of organic molecules that subsequently dissociate to form free radicals should be useful in the present method. Suitable water-soluble ceric salts include but are not limited to the nitrate, perchlorate and sulfate.

Ceric salts reportedly hydrolyze readily in aqueous solutions and are relatively strong oxidizing agents. The ease with which solubilized ceric salts hydrolyze together with the acidic nature of these salts may explain the formation of double salts in the presence of hydroxyl or ammonium ions. These double salts are preferred for use in the present method based on their availability, with ceric ammonium nitrate being particularly preferred. Many of the literature references listed in the preceding section of this specification that relate to cerium-catalyzed grafting reactions use this preferred cerium salt as the catalyst.

The present inventors have discovered that the percentage of hydrophilic organic polymer grafted to the substrate surface decreases substantially when the concentration of ceric compound in the present aqueous coating compositions is less than about 8 mmol per liter. They have also found that agglomeration and/or gelling of the hydrophilic molecules with a resultant decrease in the quality of the final coating begins to occur when the concentration of ceric compound exceeds about 32 mmol per liter.

Conditions for Forming the Grafted Hydrophilic Coating

Any of the methods and equipment conventionally used to apply liquid coating compositions can be used to apply a layer of hydrophilic polymer to a hydrophobic substrate in accordance with the present method. Low viscosity compositions are conveniently applied by dipping.

The present inventors discovered that the rate of grafting is not dependent to any substantial extent on the pH of the coating composition.

The variables affecting the rate of grafting appear to be the type and concentration of ceric compound, the type and concentration of hydrophilic polymer, the type of substrate, the temperature of the coating composition, and the residence time of the substrate in the coating composition.

Using polyvinyl alcohol as the hydrophilic polymer, the concentration of grafted polymer appears to increase with exposure time of the substrate to a maximum value. The concentration of grafted polymer is determined by washing the substrate with water, in which the hydrophilic polymer is soluble. When this maximum value has been reached, additional exposure to the coating composition results in a decrease in the quality of the coating due to agglomeration of the hydrophilic polymer. The sections of agglomerated gel are readily removed, resulting in an apparent decrease in the amount of durable coating on the surface of the substrate.

The temperature of the coating composition can range from ambient to the boiling point of the composition. The rate of grafting would be expected to be proportional to the temperature of the coating composition. For this reason it is usually preferable to maintain the temperature of the composition at a minimum of about 50° C. during the grafting reaction.

Using a polydimethylsiloxane elastomer as the substrate and a coating composition containing 10 weight percent of polyvinyl alcohol, a ceric salt concentration of 8 mmol per liter and a coating composition temperature of 100° C. optimum grafting was achieved after about 1½ hours of exposure to the coating composition. Additional exposure appeared to decrease the quality and durability of sections of the grafted coating due to formation of gel aggregates.

When it is desired to increase the thickness of the layer of hydrophilic polymer that can be deposited using the present method this can be achieved by dipping the coated substrate in a solution of the hydrophilic polymer and inducing gelation of the polymer in a manner other than by use of the present cerium compounds. The resultant hydrogel is water insoluble and therefore cannot be removed by subsequent washing of the substrate with water. Examination of the coated substrate using scanning electron microscopy reveals the presence of a coating layer on the substrate. The thickness of the coating following dipping and subsequent gelation of the hydrophilic polymer is typically from about 1 to about 2 microns.

Using the preferred polyvinyl alcohol as the coating material, conversion of the polymer to a water-insoluble hydrogel can be achieved by using a solution of the polymer in a mixture of dimethyl sulfoxide and water as the coating composition. The coated substrate is then cooled to a temperature below about 0° C. to convert the water soluble form of the polymer to a polyvinyl alcohol hydrogel. It should be noted that the water portion of the solvent does not freeze in the presence of dimethyl sulfoxide.

The following examples describe preferred embodiments of the present coating compositions and method, and should not be interpreted as limiting the scope of the invention defined in the accompanying claims. Unless otherwise specified all parts and percentages are by weight and viscosities were measured at 25° C.

EXAMPLE 1

This example demonstrates grafting of polyvinyl alcohol to a sheet of elastomeric polydimethylsiloxane.

Five samples of various shapes and known surface area were cut from a sheet of cured medical grade polydimethylsiloxane elastomer measuring about 0.1 cm in thickness. The average surface area of the samples was about 4 cm2. The samples were washed with double distilled water, dried and weighed.

Aqueous solutions of polyvinyl alcohol (PVA) were prepared by heating the required quantity of PVA exhibiting an average molecular weight of 89,000 and double distilled water at 100° C. for 1.5 hours under a nitrogen atmosphere with stirring. The samples to be coated were then added to the solution, which was stirred for an additional 10 minutes. At this time a quantity of ceric ammonium nitrate equivalent to a concentration of 4.2, 8.4, 16.9 or 32.8 mmol per liter of the PVA solution was added to the solution. Samples of the elastomer were withdrawn from the heated, stirred solutions at 30 minute intervals, washed in double distilled water and dried.

The hydrophilic nature of the substrate surface was determined by measuring the contact angle between the substrate and water and the ability of water to form a continuous layer rather than discrete droplets on the surface of the substrate.

The extent of grafting was determined by weighing each of the initial and coated substrate and inserting these values into the formula Extent of Grafting = $(W_{cs} - W_{is}) \times 10^4$/Surface Area of Substrate where $W_{cs}$ is the weight of the coated substrate and $W_{is}$ is the weight of the initial substrate measured following washing and drying.

The PVA concentration, temperature of the PVA solution in contact with the substrate, cerium salt concentration, and the extent of grafting as a function of exposure time of the substrate to the heated polyvinyl alcohol solution in the presence of the cerium compound are recorded in Table 1.

TABLE 1

| Sample No. | Temp./Conc. of PVA Soln. (°C./Wt. %) | Ce Salt Conc. mmol/L | Extent of Grafting Following n Minutes n = | | | | |
|---|---|---|---|---|---|---|---|
| | | | 30 | 60 | 90 | 120 | 150 |
| 1 | 100°/10 | 4.2 | 4.44 | 7.75 | 14.21 | NA | 31.76 |
| 2 | 70°/10 | 4.2 | 9.48 | 11.26 | 8.58 | 4.54 | 15.96 |
| 3 | 100°/10 | 8.4 | 15.87 | 19.42* | 22.81** | 19.86 | 10.73 |
| 4 | 100°/10 | 16.9 | 13.23 | 18.93 | 17.54 | 11.7 | 24.24 |
| 5C | 100°/10 | 33.8 | 5.47 | 6.95 | PVA Gels | | |
| 6C | 100°/10 | 0 | PVA removed during washing of substrate | | | | |
| 7C | 100°/10(no stir) | 8.4 | NA | 6.75 | 0.33 | 0.98 | 7.09 |
| 8 | 100°/1 | 8.4 | Substrates coated only in regions, coated regions not smooth or continuous | | | | |
| 9 | 100°/2.5 | 8.4 | 3.46 | 7.87 | NA | 9.69 | 8.56 |
| 10 | 100°/7.5 | 8.4 | 4.16 | 5.52 | 11.8 | 24.1 | 50.63 |
| 11 | 100°/15 | 8.4 | 5,81 | 5.94 | 7.27 | 11.12 | 13.22 |

*Sample used to determine protein adsorption (Example 2) and blood platelet adhesion (Example 4)
**Sample examined using scanning electron microscopy and X-ray photoelectron spectroscopy.

The procedure used to prepare the sample that was examined using the scanning electron microscope involved cutting slices from the sample and coating them with a conductive metallic layer. Both the surface of the substrate and a cross-section perpendicular to the surface were examined. Even though the surface was hydrophilic, no obvious changes in the morphology or texture of the substrate surface were apparent relative to an uncoated substrate, which is indicative of a very thin coating.

The x-ray photoelectron spectra were obtained using a magnesium anode operating at 300 watts and 14 kilovolts. The percent atomic composition observed using a normal angle of 90° for carbon, oxygen and silicon are recorded in the following table.

TABLE 2

| | Oxygen | Carbon | Silicon |
|---|---|---|---|
| Coated Sample | 29.7 | 57.0 | 18.8 |
| PDMS* Surface (Control) | 27.0 | 50.0 | 23.0 |

*Polydimethylsiloxane

Higher concentrations of oxygen and carbon relative to the polydimethylsiloxane are indicative of a layer of hydrophilic organic material on the surface of the substrate, in this instance the polyvinyl alcohol.

EXAMPLE 2

This example demonstrates the lower susceptibility of substrates coated in accordance with the present invention to protein adsorption relative to uncoated substrates.

Bovine Serum Albumin (BSA) and human fibrinogen were dissolved first in a phosphate buffered saline solution (PBS) exhibiting a pH of 7.4. The concentration of the BSA was 3.0 mg/cc and the concentration of the fibrinogen was 0.5 mg/cc. Sheets of polydimethylsiloxane (PDMS) that were coated under the conditions described for sample 3 of Example 1 in this specification were immersed in one of the two protein solutions for 3 hours at a solution temperature of 37° C., then rinsed with additional PBS to remove any weakly bonded proteins. The surface concentration of absorbed proteins was then determined using ninhydrin as described by R. McGrath in Anal. Biochem., 49, 95–102 (1972).

For comparative purposes uncoated sheets of polydimethylsiloxane that had been dipped into one of the protein solutions were analyzed using the ninhydrin test, together with sheets of polydimethylsiloxane which had been coated as described for sample 3 of example 1 but not immersed in either of the protein solutions.

The percentages of BSA and fibrinogen adsorbed on the surface of the treated substrates relative to the untreated (PDMS) control are also recorded in the following table.

TABLE 3

| EXTENT OF GRAFTING | BSA ADSORPTION* $\mu g/cm^2$ | %** BSA $\mu g/cm^2$ | FIBRINOGEN* ADSORPTION | %** FIBRINOGEN |
|---|---|---|---|---|
| 15.87 | 0.091 | 14.00 | 0.300 | 22 |
| 19.42 | 0.03 | 5.0 | 0.127 | 9 |
| 22.81 | 0.144 | 22.00 | 0.352 | 26 |
| PDMS (CONTROL) | 0.646 | — | 1.356 | — |

*Error in determinations = ±10%
**Based on 100% for PDMS control

EXAMPLE 3

This example demonstrates formation and grafting of a polyvinyl alcohol hydrogel on the surface of a natural rubber catheter using a preferred two-step process.

A glass reactor equipped with a mechanically operated stirrer, thermometer and water cooled condenser was charged with 900 cc of distilled water and 100 g. of polyvinyl alcohol having a molecular weight of 86,000 to form a 10 weight percent solution. The water was heated at 100° C. with stirring until the polymer dissolved. The reactor was then flushed with nitrogen while stirring was continued for an additional 1.5 hours.

A Foley catheter formed from natural rubber was placed in the resultant solution, following which 8.333 g. (equivalent to a concentration of 8.44 mmol/liter) of ceric ammonium nitrate was added to the solution and heating continued for an additional 1.5 hours.

The catheter was then removed from the solution and dipped into a 5 weight percent solution of polyvinyl alcohol in a 4:1 volume ratio mixture of dimethyl sulfoxide and water maintained at a temperature of 70° C.

The coated catheters were then hung in a jar so as not to contact one another or the inner surface of the jar and the jar was placed for 19 hours in a freezer maintained at a temperature of −25° C. The catheters were then placed in a container of double distilled water to extract the dimethylsulfoxide.

The apparent coefficient of friction of the surface of the coated catheter and an uncoated control was determined by measuring the force required to pull a weighted sled over the surface of the catheters while the catheters were submerged in water. The surface of the sled in contact with the catheter was coated with a layer of hydrogel to simulate natural animal tissue. The coefficients of friction of the coated and uncoated catheters were 0.054 and 0.095, respectively.

The coating could not be removed by rubbing the surface of the catheter.

EXAMPLE 4

This example describes an alternative method for applying a second layer of hydrophilic polymer to a substrate. Samples of a polydimethylsiloxane elastomer were prepared and coated with a grafted layer of polyvinyl alcohol as described in Example 1. The solution into which the samples were dipped contained 10 weight percent of polyvinyl alcohol, the concentration of ceric ammonium nitrate was 8.44 mmol/liter and the sample remained in the solution for 1.5 hours following the sample remained in the solution for 1.5 hours following addition of the ceric ammonium nitrate.

After the samples were removed from the polyvinyl alcohol/ceric ammonium nitrate solution they were dipped into a 5 weight percent solution of polyvinyl alcohol in a 4:1 volume ratio mixture of dimethyl sulfoxide and water maintained at a temperature of 70° C.

The coated samples were then spun for 30 seconds in a photo-resist spin coating apparatus manufactured by Headway Research Inc. (Model EC 101). The suction used to keep the samples on the rotating platform of the spin coating apparatus removed the coating from the surface of the sample in contact with the platform.

The samples were then placed on ceramic boat-shaped supports to minimize contact with the supports and stored in a freezer at −25° C. for 19 hours. The samples were then placed in double distilled water to remove the dimethyl sulfoxide.

Examination of the samples under a scanning electron microscope revealed a substantially uniform, continuous coating with a thickness of 1.5 microns on the major surface of the sample that was not in contact with the platform of the spin coating apparatus. No visible separation of the coating was observed.

Analysis of the samples using X-ray photoelectron spectroscopy revealed considerably less silicon (4.2 % silicon, based on total atoms using the normal angle of 90°) on the surface relative to the sample examined as described in example 1 of this specification (18.8 percent silicon under the same conditions).

The uniformity of the coating was also determined using iodine as described by M. M. Zwizk in the Journal of Applied Polymer Science, Vol. 9, pp. 2393–2424 (1965). This test is often used to determine the presence of a starch. The clear blue color that constituted a positive test for a hydroxyl-containing polymer was continuous and uniform along the entire coated surface of the sample.

Analysis of one coated sample using Fourier transform infra-red spectroscopy showed a large absorption maximum in the range from 6000 to 4400 $cm^{-1}$, indicative of a high concentration of hydroxyl groups on the surface of the sample. The spectrum remaining following normalization and subtraction of the spectrum of the treated sample from the spectrum of an untreated polydimethylsiloxane sample was a typical spectrum for polyvinyl alcohol.

EXAMPLE 5

This example demonstrates the substantial absence of blood platelet adhesion, a major factor in biocompatibility, on hydrophobic polydimethylsiloxane substrates coated in accordance with the present invention.

The platelets were separated from citrated human blood and used immediately following the separation. The platelet concentration of suspended platelets in the plasma was adjusted to $1 \times 10^8$ per $cm^3$ by dilution with 0.14 mole of sodium chloride solution, 15 mmol tris(hydroxymethyl)aminomethane hydrochloride and 5.5 mmol glucose. The pH of the resultant solution was 7.5.

One cc. portions of the platelet suspension were placed in wells of a multi-well dish and samples of the polydimethylsiloxane sheet identified by the asterisk (*) in Table 1 of the present specification were then placed in half of the wells containing the platelets. The samples were in the form of disks having a radius of 1.5 cm. Disks of uncoated polydimethylsiloxane elastomer were used for comparative purposes. The dish was then allowed to remain at a temperature of 20° C. for 20 minutes to ensure adhesion of the platelets to the surface of the test samples. The samples were then removed from the well dish, rinsed with a phosphate buffer saline (PBS) solution to remove weakly adhered platelets and fixed by soaking in a 10% buffered formalin solution for 2 hours. The samples were then rinsed with PBS, followed by a rinsing with distilled water. After drying the samples were examined using a scanning electron microscope at a magnification of 1,000.

A concentration of platelets equivalent to $2.0 \times 10^6$ per $cm^2$ was observed on the uncoated control sample. Only a very few isolated platelets were present on the sample that had been coated with a layer of polyvinyl alcohol in accordance with the present invention.

That which is claimed is:

1. A method for grafting a preformed hydrophilic organic polymer to the surface of a solid substrate consisting essentially of hydrophobic organic polymers said method comprising:

(I) contacting said substrate with an aqueous composition comprising a solubilized form of said hydrophilic organic polymer and a solubilized compound of tetravalent cerium, wherein the quantity of said compound is sufficient to promote grafting of said hydrophilic organic polymer to the surface of said substrate, (II) maintaining said substrate in contact with said composition for a period of time sufficient to graft at least a portion of said hydrophilic polymer to the surface of said substrate in the form of a substantially uniform, coherent layer, and (III) separating said substrate from said composition.

2. A method as claimed in claim 1 wherein said cerium compound contains at least one ligand selected from the group consisting of hydroxyl and amino groups, the temperature of said composition is at least 50° C., the concentration of said compounds is from 2 to 20 mmol per liter of said composition, said hydrophobic polymer polyurethane, and said hydrophilic organic polymer is selected from the group consisting of polyvinyl alcohol and polymerized half esters of a diol and an ethylenically unsaturated carboxylic acid.

3. A method as claimed in claim 2 wherein said substrate is selected from the group consisting of polyurethanes, and natural rubber, said compound is ceric ammonium nitrate, and said ethylenically unsaturated carboxylic acid is selected from a group consisting of
 (i) acrylic and
 (ii) methacrylic acid.

* * * * *